(12) United States Patent
Fitz-Coy et al.

(10) Patent No.: US 10,564,096 B2
(45) Date of Patent: Feb. 18, 2020

(54) METHOD FOR MEASURING BI-DIRECTIONAL REFLECTANCE DISTRIBUTION FUNCTION (BRDF) AND ASSOCIATED DEVICE

(71) Applicant: University of Florida Research Foundation, Inc., Gainesville, FL (US)

(72) Inventors: Norman G. Fitz-Coy, Gainesville, FL (US); Kunal Shrikant Patankar, Gainesville, FL (US); Matthew T. Moraguez, Atlantis, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 174 days.

(21) Appl. No.: 15/759,988

(22) PCT Filed: Sep. 13, 2016

(86) PCT No.: PCT/US2016/051439
§ 371 (c)(1),
(2) Date: Mar. 14, 2018

(87) PCT Pub. No.: WO2017/048674
PCT Pub. Date: Mar. 23, 2017

(65) Prior Publication Data
US 2018/0252642 A1    Sep. 6, 2018

Related U.S. Application Data

(60) Provisional application No. 62/218,062, filed on Sep. 14, 2015.

(51) Int. Cl.
*G01N 21/55* (2014.01)
*G01N 21/31* (2006.01)
*G01N 21/47* (2006.01)

(52) U.S. Cl.
CPC ............. *G01N 21/55* (2013.01); *G01N 21/31* (2013.01); *G01N 21/474* (2013.01)

(58) Field of Classification Search
CPC ............................ G01N 21/55; G01N 21/474
See application file for complete search history.

(56) References Cited

U.S. PATENT DOCUMENTS

| 5,712,701 A | 1/1998 | Clementi et al. |
| 7,075,534 B2 | 7/2006 | Cole et al. |

(Continued)

FOREIGN PATENT DOCUMENTS

| CN | 100443881 C | 12/2008 |
| CN | 1928533 B | 5/2010 |

(Continued)

OTHER PUBLICATIONS

Bowers, David L., et al., "Broadband Spectral-Polarimetric BRDF Scan System and Data for Spacecraft Materials", Proceedings of the Advanced Maui Optical and Space Surveillance Technologies Conference, Sep. 13-16, 2011, 9 pages, Wailea, Maui, Hawaii,.

(Continued)

*Primary Examiner* — Maurice C Smith
(74) *Attorney, Agent, or Firm* — Alston & Bird LLP

(57) ABSTRACT

Methods, computer program products, and corresponding devices are provided for measuring the bi-directional reflectance distribution function (BRDF) of an object. An object is positioned relative to a BRDF measurement device. The BRDF measurement device comprises a turntable coupled to a background and a light source, the turntable configured to have the object positioned thereon; and a plurality of spectrographs configured such that each of the plurality of the spectrographs captures a reflectance spectra associated with the object from a different elevation angle relative to the object. A set of spectra data is captured by illuminating the (Continued)

object with the light source; and with each spectrograph, capturing a reflectance spectra associated with the object. The turntable is rotated such that an azimuthal angle between the object and the light source is changed. The capturing and rotating steps are repeated for a predetermined set of azimuthal angles.

21 Claims, 6 Drawing Sheets

(56) References Cited

U.S. PATENT DOCUMENTS

| | | | |
|---|---|---|---|
| 7,929,142 | B2 | 4/2011 | Ben-Ezra et al. |
| 9,804,087 | B2 * | 10/2017 | Hegstrom ............ G01N 21/474 |
| 2003/0231175 | A1 * | 12/2003 | Pfister .................. G06T 15/205 345/419 |
| 2004/0001059 | A1 | 1/2004 | Pfister et al. |
| 2006/0274316 | A1 * | 12/2006 | Perquis ..................... G01J 3/46 356/446 |
| 2009/0079987 | A1 | 3/2009 | Ben-Ezra et al. |
| 2011/0276299 | A1 * | 11/2011 | Nemoto ............. G01N 21/9501 702/104 |
| 2014/0152990 | A1 * | 6/2014 | Ehbets ...................... G01J 3/50 356/405 |
| 2016/0171748 | A1 * | 6/2016 | Kohlbrenner ........... G06T 15/10 348/48 |

FOREIGN PATENT DOCUMENTS

| | | |
|---|---|---|
| CN | 102323240 A | 1/2012 |
| CN | 103115876 A | 5/2013 |
| WO | WO 2006/116386 A1 | 11/2006 |

OTHER PUBLICATIONS

Cowardin, H., et al., "NASA's Optical Measurement Program 2014", Proceedings of AMOS Technologies Conference 2014; Sep. 9-12, 2014, 10 pages, Maui, HI.

Fraunhofer Iosb, "BRDF Measurements with Robots", 2012, 6 pages, retrieved from https://www.iosb.fraunhofer.de/servlet/is/14836/ on Feb. 21, 2018,.

Hullin, Matthias B., et al., "Acquisition and Analysis of Bispectral Bidirectional Reflectance and Reradiation Distribution Functions", ACM Transactions on Graphics, Jul. 2010, pp. 97:1-97:7, vol. 29, No. 4, Article 97, ACM Digital Library.

International Searching Authority, International Search Report and Written Opinion for International Application No. PCT/US2016/051439, dated Dec. 23, 2016, 22 pages, Korean Intellectual Property Office, Republic of Korea.

Rabal, AM, et al., "Automatic Gonio-Spectrophotmeter for the Absolute Measurement of the Spectral BRDF at In- and Out-of-Plane and Retroreflection Geometries", Optomechatronic Technologies International Symposium, Oct. 2010, pp. 1-6, IOP Publishing.

Roosjen, Peter, et al., A New Setup to Measure Bidirectional Reflectance Distribution Functions, Proceedings of Workshop Sensing a Changing World, May 9-11, 2012, 9 pages, Wageningen University, The Netherlands.

Sun, Chengming, et al., "Research on the Model of Spectral BRDF for Space Target Surface Material", Optomechatronic Technologies International Symposium, Oct. 2010, pp. 1-6, IEEE.

Zhang, Wei, et al., "Measurement of Bidrectional Reflection Distribution Function on Material Surface", *Chinese Optics Letters*, Jan. 10, 2009, pp. 88-91, vol. 7, No. 1, OSA Publishing.

* cited by examiner

METHOD FOR MEASURING BI-DIRECTIONAL REFLECTANCE DISTRIBUTION FUNCTION (BRDF) AND ASSOCIATED DEVICE

CROSS REFERENCE TO RELATED APPLICATIONS

This application is a National Stage Application, filed under 35 U.S.C. § 371, of International Application No. PCT/US2016/051439, filed Sep. 13, 2016, which claims priority to U.S. Application No. 62/218,062, filed Sep. 14, 2015; the contents of both of which are hereby incorporated by reference in their entirety.

FEDERALLY SPONSORED RESEARCH OR DEVELOPMENT

This invention was made with government support under grant number NNX11AQ41G awarded by the National Aeronautics and Space Administration (NASA). The government has certain rights in the invention.

BACKGROUND

Since the launch of Sputnik 1 in 1957, many manmade objects have been launched into space. While some of those objects have traveled far beyond Earth (e.g., Voyager 1 and 2) and some of those objects have returned to Earth (e.g., Apollo 11), a large number of objects or portions of objects remain in orbit around the Earth. These objects are referred to as orbital debris. For example, orbital debris may include the non-limiting examples of derelict spacecraft, upper stages of launch vehicles, carriers for multiple payloads, debris intentionally released during spacecraft separation from its launch vehicle or during mission operations, debris created as a result of spacecraft or upper stage explosions or collisions, solid rocket motor effluents, and tiny flecks of paint released by thermal stress or small particle impacts. More than 21,000 orbital debris larger than 10 cm are known to exist. The estimated population of particles between 1 and 10 cm in diameter is approximately 500,000. The number of particles smaller than 1 cm is estimated to exceed 100 million.

In order to evaluate the risk to spacecraft (e.g., satellites, the space station, manned and unmanned missions, etc.) currently in use or planned for use, it is important to be able to identify and classify orbital debris. An important tool for identifying and/or classifying orbital debris is the use of the bi-directional reflectance distribution function (BRDF). The BRDF for a known object may be measured in ground based lab setting. A known object's BRDF may then be compared to the BRDF measured for an unknown space debris in order to identify and/or classify the unknown item. Current methods for measuring BRDFs in ground based settings rely upon robotic manipulators or handheld cameras, which is time consuming and introduces the possibility of systemic and/or random errors into the measurement. Therefore, a need exists for improved methods and corresponding devices for measuring the BRDF of a known object.

The present invention provides improved methods and associated devices for measuring the BRDF of an object.

BRIEF SUMMARY

The present invention provides a method for measuring the BRDF of an object in which two or more cameras, spectroscopes, or spectrographs (referred to as spectrographs herein) are placed in a fixed position. A light source is used to illuminate the object and each of the spectrographs captures a reflectance spectra reflected from the object. The orientation of the object with respect to the light source is changed (e.g., by rotating a turntable having the object thereon or by rotating the light source about the turntable) and the spectrographs capture another set of reflectance spectra. Additional spectra may be captured at various orientations of the object with respect to the light source as desired. The resulting spectral data may then be analyzed to calculate and/or determine the BRDF of the object.

According to one aspect of the present invention, a method for measuring bi-directional reflectance distribution function (BRDF) of an object is provided. In example embodiments, the method comprises (a) positioning an object relative to a BRDF measurement device, (b) capturing a set of spectra data, (c) rotating the turntable such that an azimuthal angle between the object and the light source is changed, and (d) repeating steps (b) and (c) for a predetermined set of azimuthal angles. In example embodiments, the BRDF measurement device comprises a turntable coupled to a background and a light source, the turntable configured to have the object positioned thereon; and a plurality of spectrographs configured such that each of the plurality of the spectrographs captures a reflectance spectra associated with the object from a different elevation angle relative to the object. The set of spectra data may be captured by illuminating the object with the light source; and with each spectrograph, capturing a reflectance spectra associated with the object.

According to another aspect of the present invention, a bi-directional reflectance distribution function (BRDF) measurement device is provided. In example embodiments, the BRDF measurement device comprises a turntable configured to having an object positioned thereon; a background; a light source; a spectrograph support; and a plurality of spectrographs. Each spectrograph is secured to the spectrograph support and is configured to capture a reflectance spectra of an object placed on the turntable. The light source and the background are coupled to the turntable such that the position of the light source with respect to the background is fixed and the orientation of the turntable with respect to the light source can be changed.

According to yet another aspect of the present invention, a computer program product for measuring a bi-directional reflectance distribution function (BRDF) of an object is provided. In example embodiments, the computer program product comprises at least one non-transitory computer-readable storage medium having computer-readable program code portions stored therein. The computer-readable program code portions comprise a first executable program portion configured to capture a set of spectra data corresponding to the object. The object is positioned relative to a BRDF measurement device. The BRDF measurement device comprises a turntable coupled to a background and a light source and is configured to have the object positioned thereon; and a plurality of spectrographs configured such that each of the plurality of spectrographs captures a reflectance spectra associated with the object. Capturing the set of spectra data corresponding to the object comprises causing the object to be illuminated by the light source; and causing each spectrograph to capture a reflectance spectra associated with the object. The computer-readable program code portions further comprise a second executable program portion configured to cause the turntable to rotate such that an azimuthal angle between the object and the light source is changed; and a third executable program portion configured to cause the first executable program portion and the second executable program portion to be executed for each azimuthal angle of a predetermined set of azimuthal angles.

BRIEF DESCRIPTION OF THE DRAWINGS

Figure 1:
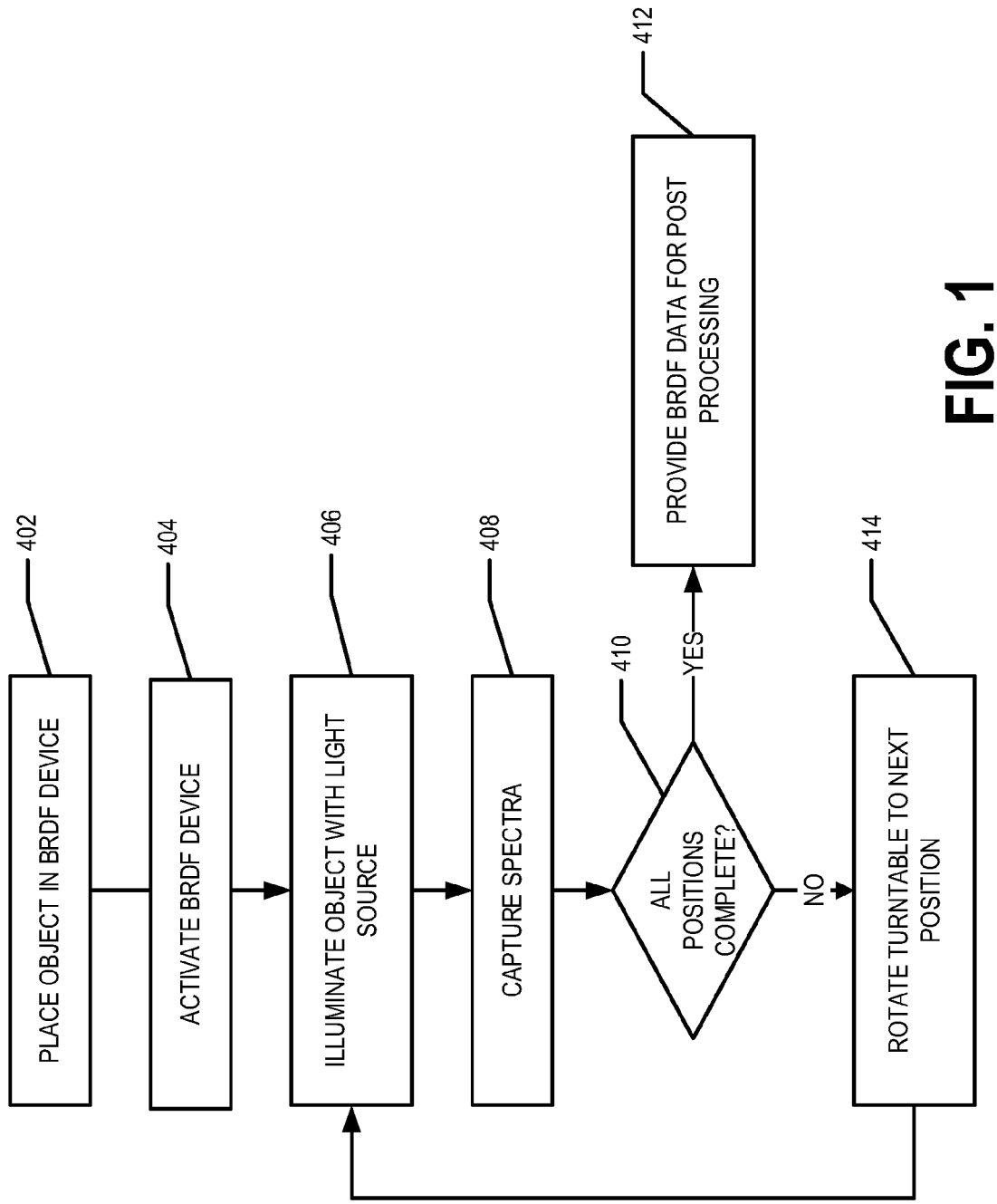
Figure 2:
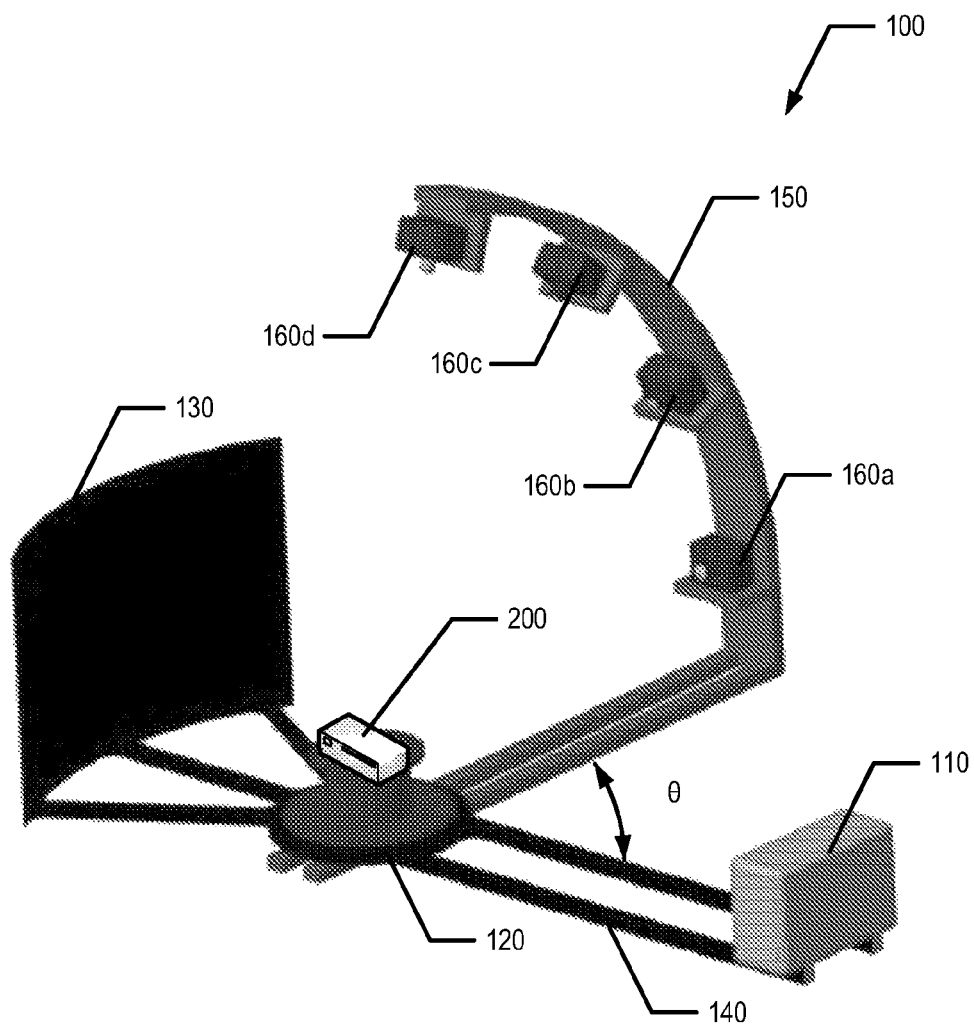
Figure 3:
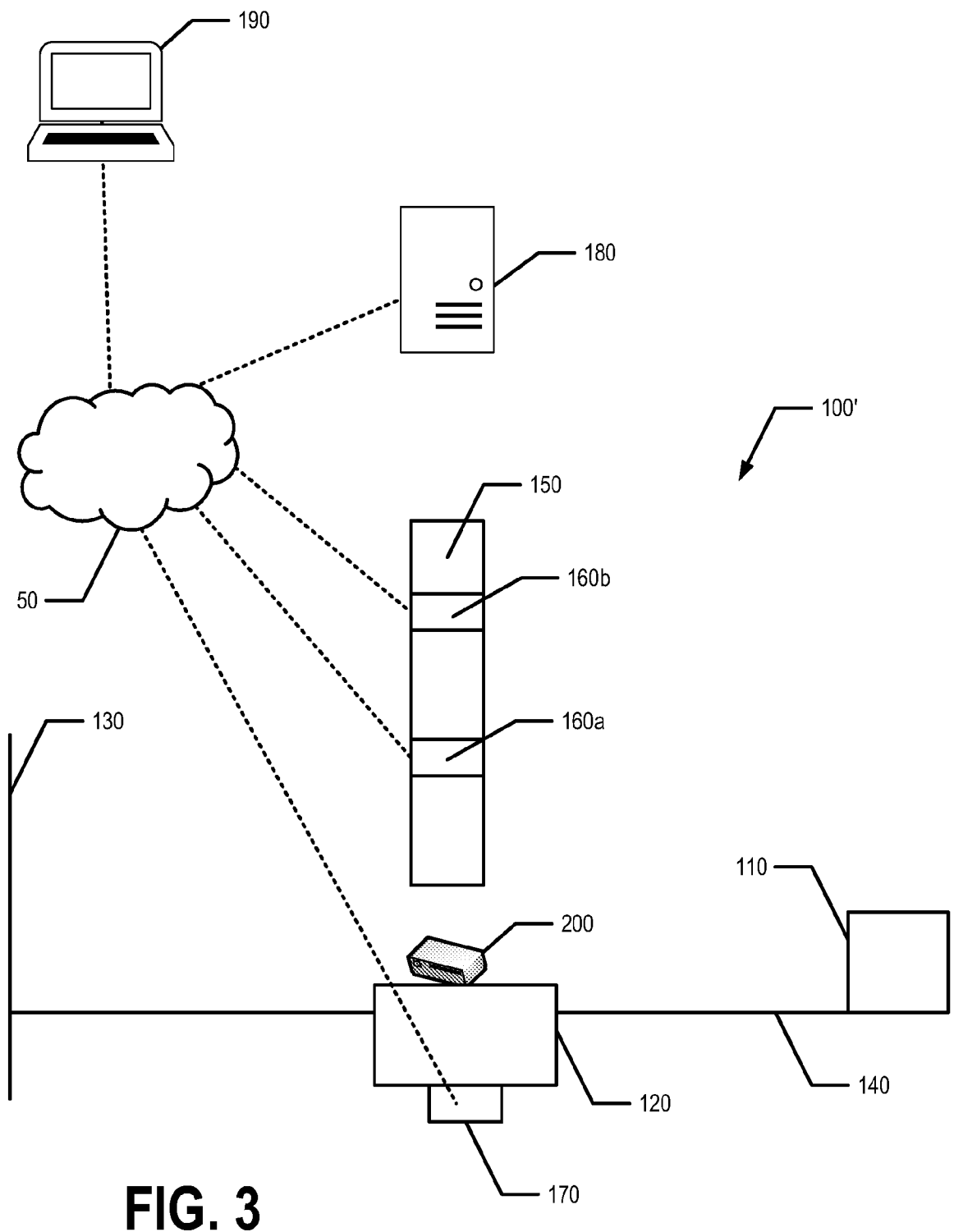
Figure 4:
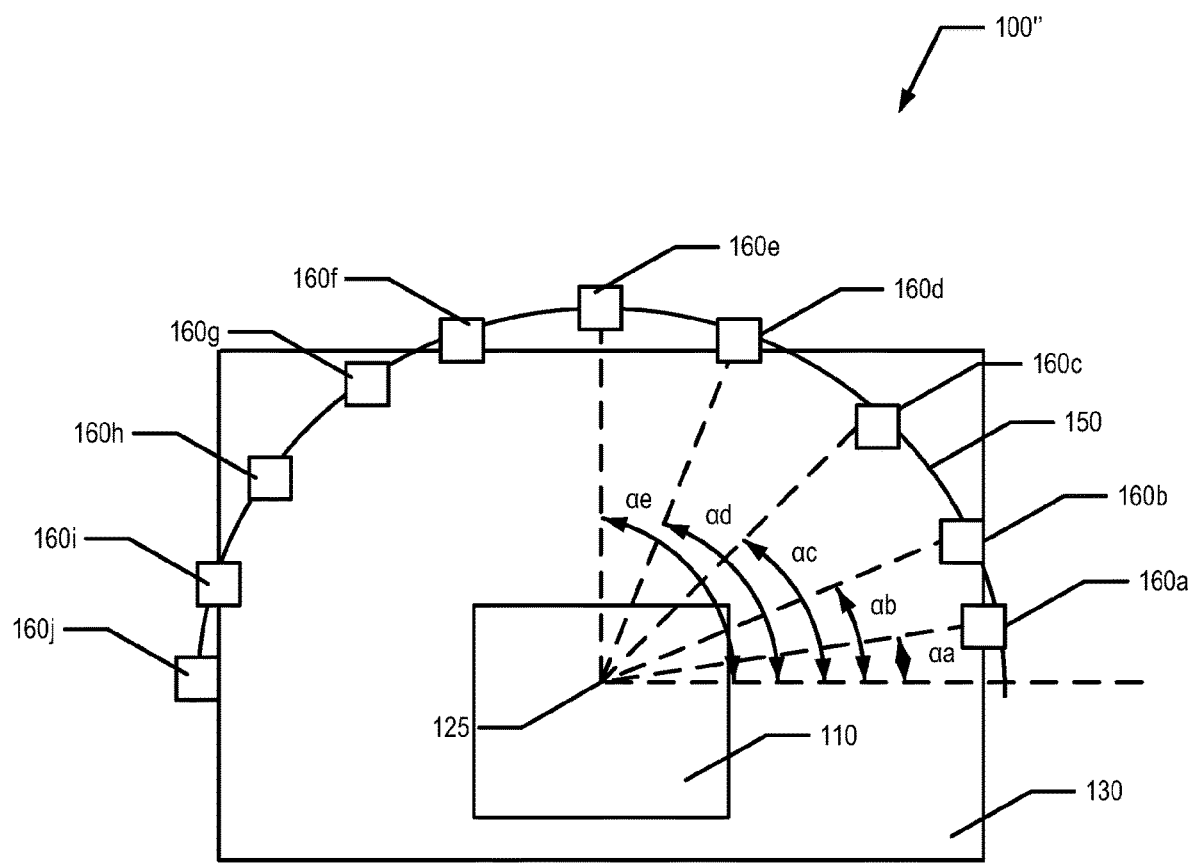
Figure 5:
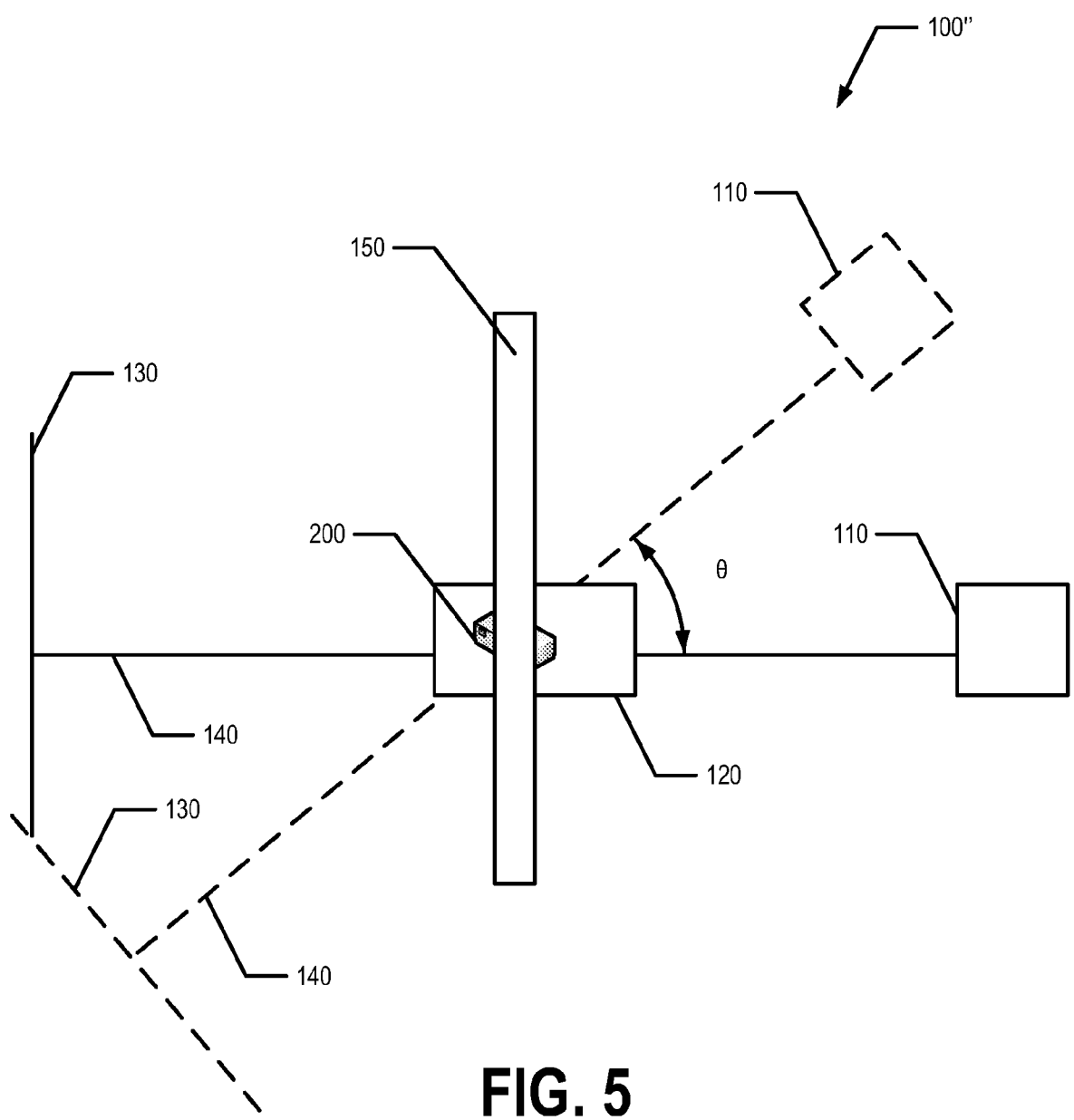
Figure 6:
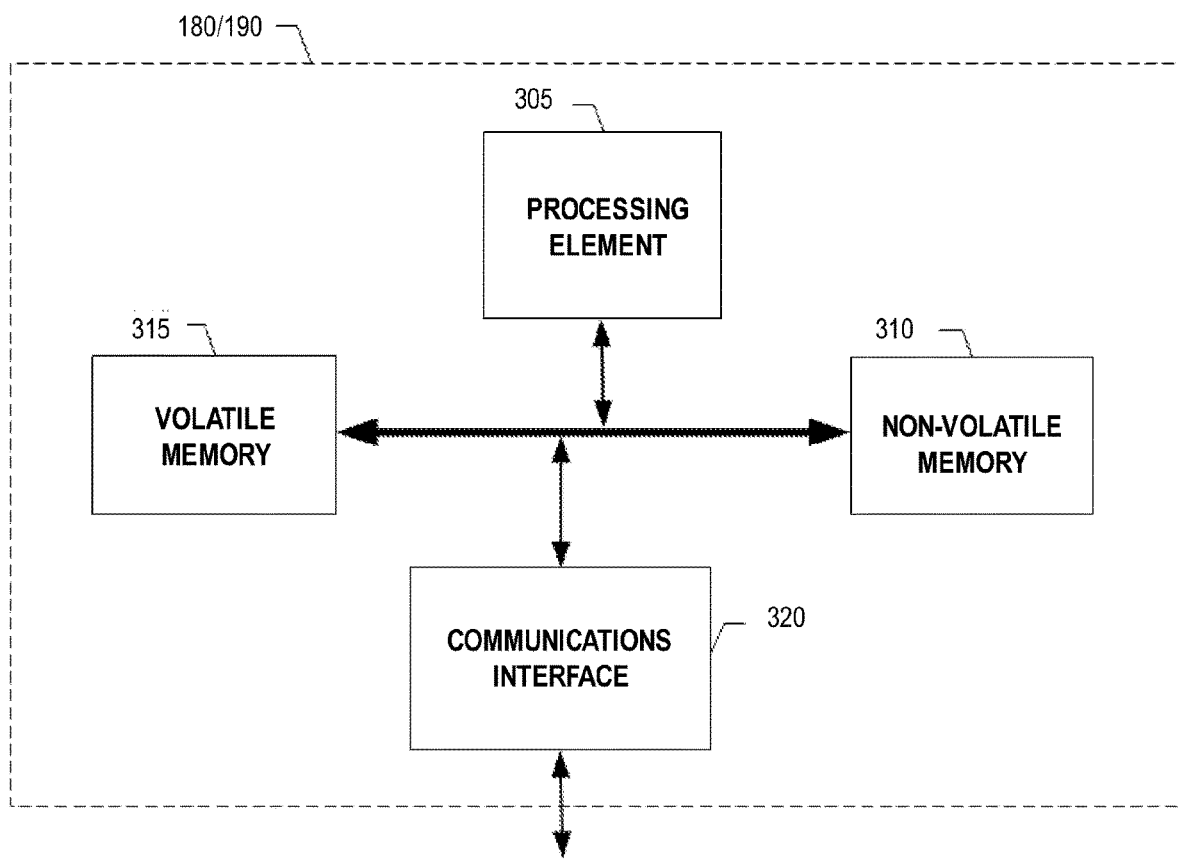

Having thus described the invention in general terms, reference will now be made to the accompanying drawings, which are not necessarily drawn to scale, and wherein:

FIG. 1 provides a flowchart of various procedures and process that may be completed in accordance with an exemplary embodiment of the present invention;

FIG. 2 provides a perspective view of a BRDF measurement device, in accordance with an exemplary embodiment of the present invention;

FIG. 3 is a side-view block diagram of a BRDF measurement device, in accordance with an exemplary embodiment of the present invention;

FIG. 4 is a different side view of BRDF measurement device, in accordance with an exemplary embodiment of the present invention;

FIG. 5 is a top view of a BRDF measurement device, in accordance with an exemplary embodiment of the present invention; and FIG. 6 is a block diagram of a control system and/or processing system, in accordance with an exemplary embodiment of the present invention.

DETAILED DESCRIPTION OF VARIOUS EMBODIMENTS

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

I. MEASURING BRDF

The present invention provides methods for measuring a BRDF of an object and associated devices. FIG. 1 provides a flowchart illustrating various processes and procedures that may be completed in accordance with various embodiments of the present invention. Starting at step 402, an object is placed in a BRDF measurement device. For example, as shown in FIG. 2, the object 200 may be placed on a turntable 120 of a BRDF measurement device 100.

FIGS. 2-5 illustrate various views of example BRDF measurement devices 100, 100', and 100". In various embodiments, a BRDF device 100, 100', 100" may comprise a turntable 120, a light source 110, a background 130, a bracket 140, a spectrograph support 150, and a plurality of spectrographs 160 (e.g., two or more). The turntable 120 may be configured to have an object 200 placed thereon. The light source 110 may be configured to illuminate an object 200 placed on the turntable 120. The background 130 may be configured to eliminate reflections from interfering with the reflectance spectra to be captured by the spectrographs. The bracket 140 may be configured to maintain the light source 110 and the background 130 in a fixed position with respect to each other and configured to allow the relative orientation of the object 200 and the light source 110 to be changed (e.g., allow rotation through azimuthal angle θ). The spectrograph support 150 may be configured to hold a plurality of spectrographs 160 (e.g., 160a-j) in a fixed position with respect to the turntable 120. Each of the plurality of spectrographs 160 (e.g., 160a-j) may be configured to capture a reflectance spectra and provide that spectra to a processing device 180 via a direct wired or wireless connection and/or via a wired or wireless network 50.

Various embodiments of the BRDF measurement device 100' may further comprise a control device 190, a processing device 180, and a motor 170. The control device 190 may be configured to control the motor 170 to rotate the bracket 140 with respect to the turntable 120 and/or the turntable 120 with respect to the bracket 140. The control device 190 may be further configured to operate the light source 110, causing the light source to illuminate the object 200, and operate the plurality of spectrographs 160 (e.g., 160a-j) to capture reflectance spectra. The control device 190 may be configured to communicate with the motor 170, the light source 110, and/or the plurality of the spectrographs 160 (e.g., 160a-j) via direct wired or wireless connections and/or via a wired or wireless network 50. The processing device 180 may be configured to process spectra captured by each of the plurality of spectrographs 160 (e.g., 160a-j) and/or other reflectance data (e.g., azimuthal angle θ between a reference point on the object 200 or the turn table 120 and the light source 110, the elevation angle α of the spectrograph that captured the particular spectra, and/or the like). Various embodiments of the BRDF measurement device 100, 100', and 100" will be discussed in more detail elsewhere herein.

Returning to FIG. 1, at step 404, the BRDF measurement device 100, 100', 100" may be activated. For example, a user may select a start button displayed via a graphical user interface displayed by the control device 190. In another embodiment, the user may activate a hardware switch associated with the control device 190, and/or the like. As should be understood various methods may be used to activate the BRDF measurement device 100, 100', 100".

At step 406, the object 200 placed on the turntable 120 is illuminated by light emitted by the light source 110. For example, the control device 190 may cause the light source 110 to emit a light in the direction of the object 200. In various embodiments, the light source 110 may illuminate the object 200 for a predetermined time period (e.g., a fraction of a second, a second, a fraction of a minute, a minute, and/or the like), until the reflectance spectra have been captured by the spectrographs 160 (e.g., 160a-j), and/or the like.

At step 408, each of the plurality of spectrographs 160 (e.g., 160a-j) capture a reflectance spectra. For example, light emitted by the light source 110 may be reflected by the object 200. Each spectrograph may capture the reflectance spectra reflected at the elevation angle α of that spectrograph. For example, spectrograph 160a captures the reflectance spectra reflected into the elevation angle αa, as shown in FIG. 4. In various embodiments, each spectrograph 160 (e.g., 160a-j) may provide the captured spectra to the control system 190 or the processing system 180. The control system 190 and/or processing system 180 may associate each received spectra with location data (e.g., the elevation angle α of the capturing spectrograph, the azimuthal angle θ of the light source with respect to the object, and/or the like) and/or other data to compile reflectance data.

Continuing with FIG. 1, at step 410, it is determined if spectra have been captured at each desired position. For example, the control system 190 may determine if spectra have been captured at each desired position. For example, it may be desired to capture spectra at each of a predetermined set of azimuthal angles $\{\theta_n | \text{n a positive integer}\}$. In various embodiments, the predetermined set of azimuthal angles $\{\theta_n\}$ are regularly spaced. In other embodiments, the increments between $\theta_i$, $\theta_{i+1} \in \{\theta_n\}$ are not uniform. Thus, it may be determined if spectra has been captured at each $\theta_n$. If spectra have been captured at each desired position, the reflectance data may be provided to the processing system 180 for post processing and for calculating/determining the BRDF for the object based on the reflectance data at step 412. In various embodiments, the reflectance data may comprise at least some of the captured spectra, position information associated with each spectra (e.g., the elevation angle $\alpha$ at which the spectra was captured and the azimuthal angle $\theta$ at which the spectra was captured, and/or the like).

If, at step 410, it is determined that spectra have not been captured at each desired position, the method continues to step 414. At step 414, the azimuthal angle is changed from the current azimuthal angle $\theta_i$ to the subsequent azimuthal angle $\theta_{i+1}$. For example, the motor may be activated (e.g., by the control system 190) to change from the current azimuthal angle $\theta_i$ to the subsequent azimuthal angle $\theta_{i+1}$. In various embodiments, $\theta_i$, $\theta_{i+1} \in \{\theta_n\}$. The method then returns to step 406.

In certain embodiments, the measurement of the BRDF device according to the method of FIG. 1 and via the devices illustrated in FIGS. 2-5 may be at least in part computer-implemented in conjunction with the control device 190 and/or the processing device 180 and/or additional elements, as described previously herein. For example, in one aspect of the invention, a program element may be provided and configured and arranged such that, when executed on a computer, the method as described herein is implemented. The program element may be installed on a computer readable storage medium. The computer readable storage medium and the program element, which may comprise computer-readable program code portions embodied thereon, may further be contained within a non-transitory computer program product. The computer readable storage medium is thus likewise non-transitory in nature and excludes signals per se. Further details in this regard are provided elsewhere herein.

II. BRDF MEASUREMENT DEVICE

Various embodiments of the present invention provide a BRDF measurement device configured for measuring the BRDF of an object via a method of the present invention. As noted above, FIGS. 2-5 provide various views of some embodiments of a BRDF measurement device 100, 100', 100" in accordance with embodiments of the present invention. Various components of the BRDF measurement device 100, 100', 100" will now be described in detail.

In various embodiments, the BRDF measurement device 100, 100', 100" comprises a light source 110 configured to illuminate an object 200 placed on the turntable 120. In various embodiments, the light source 110 is a solar simulator. For example, the light source 110 may be configured to simulate a solar spectrum such that the reflectance spectra captured are indicative of the reflectance spectra of the object when illuminated by the sun. In various embodiments, the light source 110 is a xenon arc lamp based solar simulator. In various embodiments, the light source has a beam divergence of 0.5 degrees. In other embodiments the light source may have a beam divergence of greater than or less than 0.5 degrees.

In various embodiments, the light source 110 is secured to bracket 140. In various embodiments, the bracket 140 is configured to allow the light source 110 rotate with respect to the turntable 120. For example, as shown in FIG. 5, a set of reflectance spectra may be captured with the light source 110 in a first position with respect to the turntable 120, shown by the solid lines. The light source 110 may then be rotated through an azimuthal angle $\theta$ to a second position, shown by the dashed lines. Another set of reflectance spectra may then be captured while the light source 110 is illuminating the object 200 from the second position. Thus, in various embodiments, the object 200 and turntable 120 are fixed with respect to the spectrograph support 150 and the light source 110 is configured to rotate about the turntable 120. In various embodiments, the turntable 120 is configured to rotate with respect to the spectrograph support 150 and the light source 110. In some such embodiments, the position of the light source is fixed with respect to the spectrograph support 150 and in other such embodiments, the light source 110 may not be fixed with respect to the spectrograph support 150. In various embodiments, the control system 190 may control the rotation of the turntable 120 or the bracket 140 by controlling a motor 170 configured to rotate the turntable 120 or the bracket 140 about the turntable 120.

In various embodiments, the BRDF measurement device 100, 100', 100" may comprise a background 130. The background 130 may be configured to prevent reflections of the light emitted from the light source 110 from being incident upon the object 200 or the spectrographs 160 (e.g., 160a-j). In various embodiments, the background 130 may be fixed to the bracket 140. For example, the background 130 may be positioned directly across the turntable 120 from the light source 110. For example, if the light source 110 is at azimuthal angle $\theta$, the background 130 is at azimuthal angle $\theta+180°$. In various embodiments, the background 130 is black and/or otherwise configured for light absorption.

In various embodiments, the BRDF measurement device 100, 100', 100" comprises a spectrograph support 150. In various embodiments, the spectrograph support 150 may be fixed with respect to the turntable 120 or the light source 110. In one embodiment, the turntable 120 and/or light source 110 may be fixed and the spectrograph support 150 may be rotated to different azimuthal angles about the turntable 120 by the motor 170. In various embodiments, the spectrograph support 150 is configured to hold a plurality (e.g., two or more) spectrographs 160 (e.g., 160a-j) at fixed, predetermined elevation angles. For example, as shown in FIG. 4, spectrograph 160a may be fixed at elevation angle $\alpha a$, spectrograph 160b may be fixed at elevation angle $\alpha b$, etc. In one embodiment, the elevation angles may be adjusted before starting the BRDF capturing sequence for the object 200. The spectrograph support 150 may be configured to support the plurality of spectrographs 160 (e.g., 160a-j) such that each spectrograph is directed toward the object 200 and/or turntable 120 such that the spectrograph is positioned to capture the spectra reflected off of the object 200. In various embodiments, the spectrograph support 150 is configured to support the plurality of spectrographs 160 (e.g., 160a-j) such that the spectrographs are equidistant from the turntable center 125, an expected center of the object 200, and/or the like. Thus, in various embodiments, the spectrograph support 150 may be shaped as a circular arc. In other embodiments, the spectrograph support 150 may be shaped as an elliptical arc. The arc (circular, or elliptical) subtends an angle $\varphi$. The angle $\varphi$ may be fairly small (e.g., 10-45°), fairly large (e.g., approximately 180°), or any angle therebetween (e.g., approximately 90°, approximately 135°, and/or the like).

In various embodiments, the spectrographs 160 (e.g., 160a-j) may be evenly distributed along the spectrograph support 150. For example, the elevation angles {αn|n spectrographs} may be a multiple of a set separation angle Δα. For example, the elevation angle αi of spectrograph i may be either i*Δα or (i−1)*Δα, depending on whether the first spectrograph is positioned at an elevation angle of Δα or at 0°. In other embodiments, the spectrographs 160 (e.g., 160a-j) may be irregularly distributed along the spectrograph support 150. For example, the elevation angle αi of spectrograph i may be α(i−1)+Δαi, wherein α(i−1) is the elevation angle of spectrograph i−1 and Δαi is the separation angle between elevation angle α(i−1) and elevation angle αi. For example, in one embodiment, a first spectrograph is positioned at an elevation of 5°, the second spectrograph is positioned at an elevation angle of 20°, the third spectrograph is positioned at an elevation angle of 45°, the fourth spectrograph is positioned at an elevation angle of 55°, and a fifth spectrograph is positioned at an elevation angle of 90°. Various other spectrograph placements may be used as appropriate for the application.

In various embodiments, each spectrograph 160 (e.g., 160a-j) is configured to capture a spectra. For example, each spectrograph 160 (e.g., 160a-j) may be configured to capture light emitted by the light source 110 and reflected of the object 200 into the elevation angle at which the spectrograph is positioned. In various embodiments, each spectrograph 160 (e.g., 160a-j) may comprise a grating, a charge coupled-device (CCD) camera, other camera, and/or the like.

In various embodiments, each spectrograph 160 (e.g., 160a-j) is configured to provide spectra to a control system 190 or a processing system 180 for post processing by the processing system 180. In some embodiments, the control system 190 and the processing system 180 are integrated into one computing system. In various embodiments, the control system 180 and/or the processing system 190 may comprise one or more processors, one or more computer-readable storage devices (e.g., volatile and/or non-volatile memory), and executable code portions stored by the one or more computer-readable storage devices. The executable code portions may comprise computer code configured to operate the BRDF (e.g., cause the light source 110 to illuminate the object 200, cause the plurality of spectrographs 160 (e.g., 160a-j) to capture reflectance spectra and/or provide reflectance data to the control system 190 or the processing system 180, cause the bracket 140 to be rotated about the turntable 120, process the reflectance data to calculate/determine the BRDF for the object 200, and/or the like).

As shown by the dotted lines in FIG. 3, the control system 190 and/or processing system 180 may be in communication with the motor 170, the light source 110, each spectrograph 160 (e.g., 160a-j), other computing devices, and/or the like. The communication may be performed via a direct wired or wireless connection or via a wired or wireless network 50.

III. COMPUTER PROGRAM PRODUCTS, METHODS, AND COMPUTING ENTITIES

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY CONTROL SYSTEM

FIG. 6 provides a schematic of a control system 190 according to one embodiment of the present invention. In example embodiments, the control system 190 may be a computing device configured to control the motor 170, the azimuthal angle θ, the capturing of reflectance spectra by the one or more spectrographs 160 (e.g., 160a-j), the light source 110, and/or the like. In general, the terms computing entity, computer, entity, device, system, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the control system 190 may include one or more communications interfaces 320 for communicating with various computing entities, such as by communicating data, content, information, and/or similar terms used herein interchangeably that can be transmitted, received, operated on, processed, displayed, stored, and/or the like. For instance, the control system 190 may communicate with the motor 170, the spectrographs 160 (e.g., 160a-j), the light source 110, the processing system 180, and/or the like, and/or the like.

As shown in FIG. 6, in one embodiment, the control system may include or be in communication with one or more processing elements 305 (also referred to as processors, processing circuitry, processing device, and/or similar terms used herein interchangeably) that communicate with other elements within the control system 190 via a bus, for example. As will be understood, the processing element 305 may be embodied in a number of different ways. For example, the processing element 305 may be embodied as one or more complex programmable logic devices (CPLDs), microprocessors, multi-core processors, coprocessing entities, application-specific instruction-set processors (ASIPs), microcontrollers, and/or controllers. Further, the processing element 305 may be embodied as one or more other processing devices or circuitry. The term circuitry may refer to an entirely hardware embodiment or a combination of hardware and computer program products. Thus, the processing element 305 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 305 may be configured for a particular use or configured to execute instructions stored in volatile or non-volatile media or otherwise accessible to the processing element 305. As such, whether configured by hardware or computer program products, or by a combination thereof, the processing element 305 may be capable of performing steps or operations according to embodiments of the present invention when configured accordingly.

In one embodiment, the control system 190 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 310, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The terms database, database instance, database management system, and/or similar terms used herein interchangeably may refer to a structured collection of records or data that is stored in a computer-readable storage medium, such as via a relational database, hierarchical database, and/or network database.

In one embodiment, the control system 190 may further include or be in communication with volatile media (also referred to as volatile storage, memory, memory storage, memory circuitry and/or similar terms used herein interchangeably). In one embodiment, the volatile storage or memory may also include one or more volatile storage or memory media 315, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 305. Thus, the databases, database instances, database management systems, data, applications, programs, program modules, scripts, source code, object code, byte code, compiled code, interpreted code, machine code, executable instructions, and/or the like may be used to control certain aspects of the operation of the control system 190 with the assistance of the processing element 305 and operating system.

As indicated, in one embodiment, the control system 190 may also include one or more communications interfaces 320 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the control system 190 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1xRTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Bluetooth protocols, Wibree, Home Radio Frequency (HomeRF), Simple Wireless Abstract Protocol (SWAP), wireless universal serial bus (USB) protocols, and/or any other wireless protocol.

Although not shown, the control system 190 may include or be in communication with one or more input elements, such as a keyboard input, a mouse input, a touch screen/display input, motion input, movement input, audio input, pointing device input, joystick input, keypad input, and/or the like. The control system 190 may also include or be in communication with one or more output elements (not shown), such as audio output, video output, screen/display output, motion output, movement output, and/or the like.

As will be appreciated, one or more of the control system's 190 components may be located remotely from other control system 190 components, such as in a distributed system. Furthermore, one or more of the components may be combined and additional components performing functions described herein may be included in the control system 190. Thus, the control system 190 can be adapted to accommodate a variety of needs and circumstances. As will be recognized, these architectures and descriptions are provided for exemplary purposes only and are not limiting to the various embodiments.

V. EXEMPLARY PROCESSING SYSTEM

In one embodiment, a processing system 190 may be a computing device configured to process one or more captured reflectance spectra to determine, calculate, compute, and/or the like at least a portion of a BRDF for an object 200. For example, the processing system 190 may be configured to receive one or more reflectance spectra captured by at least one of the plurality of spectrographs 160 (e.g., 160a-j) and provided by the spectrograph(s) and/or the control system 190. The processing system 190 may then process, analyze, and/or the like the received reflectance spectra to determine, calculate, compute, and/or the like at least a portion of a BRDF for the object 200. In one embodiment, a processing system 180 may include one or more components that are functionally similar to those of the control system 190. For example, in one embodiment, the processing system 180 may include one or more processing elements (e.g., CPLDs, microprocessors, multi-core processors, coprocessing entities, ASIPs, microcontrollers, and/or controllers), one or more display device/input devices (e.g., including user interfaces), volatile and non-volatile storage or memory, and/or one or more communications interfaces. For example, the user interface may be a user application, browser, user interface, interface, and/or similar words used herein interchangeably executing on and/or accessible via the processing system 180 to interact with and/or cause display of information, as described herein. This may also enable the processing system 180 to communicate with various other computing entities, such as the control system 190, and/or various other computing entities. As will be recognized, these architectures and descriptions are provided for exemplary purposes only and are not limiting to the various embodiments. For example, in an example embodiment, the control system 190 and the processing system 180 are combined into one computing entity.

VI. CONCLUSION

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for measuring bi-directional reflectance distribution function (BRDF) of an object, the method comprising the steps of:
   (a) positioning an object relative to a BRDF measurement device, the BRDF measurement device comprising:
      (i) a turntable coupled to a background and a light source, the turntable configured to have the object positioned thereon; and
      (ii) a plurality of spectrographs configured such that each of the plurality of the spectrographs captures a reflectance spectra associated with the object from a different elevation angle relative to the object;
   (b) capturing a set of spectra data by:
      (i) illuminating the object with the light source; and
      (ii) with each spectrograph, capturing a reflectance spectra associated with the object;

(c) rotating the turntable such that an azimuthal angle between the object and the light source is changed; and
(d) repeating steps (b) and (c) for a predetermined set of azimuthal angles.

2. The method of claim 1, further comprising the steps of:
providing reflectance data to a computing device, the reflectance data comprising a set of spectra data for each angle of the predetermined set of azimuthal angles; and
processing the reflectance data to determine the BRDF for the object.

3. The method of claim 1, wherein each of the spectrographs are secured to a spectrograph support.

4. The method of claim 3, wherein rotating the turntable comprises changing the position of the light source and the background with respect to the spectrograph support while maintaining the object in a fixed position with respect to the spectrograph support.

5. The method of claim 3, wherein rotating the turntable comprises at least one of (a) changing the orientation of the object with respect to the light source or (b) changing the orientation of the object with respect to the spectrograph support.

6. A bi-directional reflectance distribution function (BRDF) measurement device comprising:
a turntable configured to having an object positioned thereon;
a background;
a light source;
a spectrograph support; and
a plurality of spectrographs, each spectrograph secured to the spectrograph support and configured to capture a reflectance spectra of an object placed on the turntable, wherein the light source and the background are coupled to the turntable such that the position of the light source with respect to the background is fixed and the orientation of the turntable with respect to the light source can be changed.

7. The BRDF measurement device of claim 6, wherein the spectrograph support defines an arc of 180 degrees.

8. The BRDF measurement device of claim 6, wherein the spectrograph support defines an arc of 90 degrees.

9. The BRDF measurement device of claim 6, wherein the plurality of spectrographs are evenly distributed along the spectrograph support.

10. The BRDF measurement device of claim 6, wherein the plurality of spectrographs are irregularly distributed along the spectrograph support.

11. The BRDF measurement device of claim 6, wherein each of the plurality of spectrographs are equidistant from at least one of a center point of the turntable or a center point of an object placed on the turntable.

12. The BRDF measurement device of claim 6, wherein each spectrograph is in communication with a computing system configured to process spectra captured by at least one of the plurality of spectrographs.

13. The BRDF measurement device of claim 6, further comprising a motor configured to rotate the turntable such that the azimuthal angle between the object and the light source is changed by a predetermined angle and in accordance with at least one of a predetermined timing schedule, based on feedback from a control or processing device, or after a set of spectra is captured.

14. The BRDF measurement device of claim 13, further comprising a control device configured to control the operation of the motor, the light source, and the spectrographs to capture a reflectance data, the reflectance data comprising a plurality of sets of spectra, each set of spectra corresponding to a particular orientation of the light source in respect to an object placed on the turntable.

15. The BRDF measurement device of claim 6, wherein the background and the light source are coupled to the turntable by a bracket configured to allow the background and the light source to rotate around the turntable while maintaining the background in a fixed spatial relationship with the light source.

16. The BRDF measurement device of claim 6, wherein each of the plurality of spectrographs is in a fixed position with respect to the turntable.

17. The BRDF measurement device of claim 6, wherein each of the plurality of spectrographs comprise a grating and a CCD camera.

18. The BRDF measurement device of claim 6, wherein each of the plurality of spectrographs is in communication with a computing system and each of the plurality of spectrographs is configured to provide captured spectra data to the computing system.

19. The BRDF measurement device of claim 6, wherein each of the plurality of spectrographs is in communication with a computing system and each of the plurality of spectrographs is configured to capture spectra data in response to receiving a trigger signal from the computing system.

20. The BRDF measurement device of claim 6, further comprising:
a motor; and
a computing system in communication with the motor, wherein the motor is configured to rotate the light source through a predetermined azimuthal angle about the turntable in response to receiving a trigger signal from the computing system.

21. A computer program product for measuring a bi-directional reflectance distribution function (BRDF) of an object, the computer program product comprising at least one non-transitory computer-readable storage medium having computer-readable program code portions stored therein, the computer-readable program code portions comprising at least one executable program portion configured to:
capture a set of spectra data corresponding to the object, the object positioned relative to a BRDF measurement device, the BRDF measurement device comprising:
(i) a turntable coupled to a background and a light source, the turntable configured to have the object positioned thereon; and
(ii) a plurality of spectrographs configured such that each of the plurality of spectrographs captures a reflectance spectra associated with the object;
wherein capturing the set of spectra data corresponding to the object comprises:
(a) causing the object to be illuminated by the light source; and
(b) causing each spectrograph to capture a reflectance spectra associated with the object; and
cause the turntable to rotate such that an azimuthal angle between the object and the light source is changed; and
cause the capturing and rotating to be executed for each azimuthal angle of a predetermined set of azimuthal angles.

* * * * *